United States Patent [19]

Husted

[11] Patent Number: 5,059,203

[45] Date of Patent: Oct. 22, 1991

[54] POWERED MICROSURGICAL TOOL

[76] Inventor: Royce H. Husted, 711 Lakeside Dr., Wheaton, Ill. 60187

[21] Appl. No.: 352,870

[22] Filed: May 17, 1989

[51] Int. Cl.$^5$ .............................................. A61B 17/32
[52] U.S. Cl. ...................................... 606/159; 606/170
[58] Field of Search ............... 606/106, 107, 159, 170, 606/171; 604/22, 27, 35, 46, 49, 52, 53

[56] References Cited

U.S. PATENT DOCUMENTS

| | | | |
|---|---|---|---|
| 3,937,222 | 2/1976 | Banko | 606/170 |
| 4,631,052 | 12/1986 | Kensey | 604/22 |
| 4,646,736 | 3/1987 | Auth | 606/159 |
| 4,649,919 | 3/1987 | Thimsen et al. | 606/159 |
| 4,669,469 | 6/1987 | Gifford, III et al. | 606/170 X |
| 4,729,763 | 3/1988 | Henrie | 604/22 |
| 4,747,406 | 5/1988 | Nash | 606/159 |
| 4,754,755 | 7/1988 | Husted | 606/159 |
| 4,772,258 | 9/1988 | Marangoni et al. | 604/22 |
| 4,842,579 | 6/1989 | Shiber | 604/22 |
| 4,850,354 | 7/1989 | McGurk-Burleson et al. | 606/170 |
| 4,850,957 | 7/1989 | Summers | 604/22 |
| 4,857,046 | 8/1989 | Stevens et al. | 604/22 |
| 4,894,051 | 1/1990 | Shiber | 604/22 |
| 4,895,560 | 1/1990 | Papantonakos | 604/22 |

*Primary Examiner*—Mickey Yu
*Assistant Examiner*—Michael Brown
*Attorney, Agent, or Firm*—Nicholas A. Camasto

[57] ABSTRACT

A miniature rotatable work wheel includes a cutting blade that is integrally formed with a drive hub and axle and mounted for rotatable movement at the end of a casing member. The casing member is a multi lumen tube. A single monofilament drive line is looped around the drive hub and extends through separate lumens of the multi lumened tube to a source of drive power. The drive hub has sharp corners and creates a positive drive connection with the monofilament drive line at the cutting blade. The hub also has a cupped cross section for inhibiting the monofilament drive line from riding off the hub. A drag load is applied to the payout end of the monofilament drive line close to the drive hub. The miniature powered surgical tool may be used with a catheter to incise occlusions in blood vessels for performing enhanced balloon angioplasties. It may also be used by a surgeon as a power scalpel. A milling type abrasive work wheel is disclosed as is an axially rotatable work wheel and a low friction drive system.

11 Claims, 3 Drawing Sheets

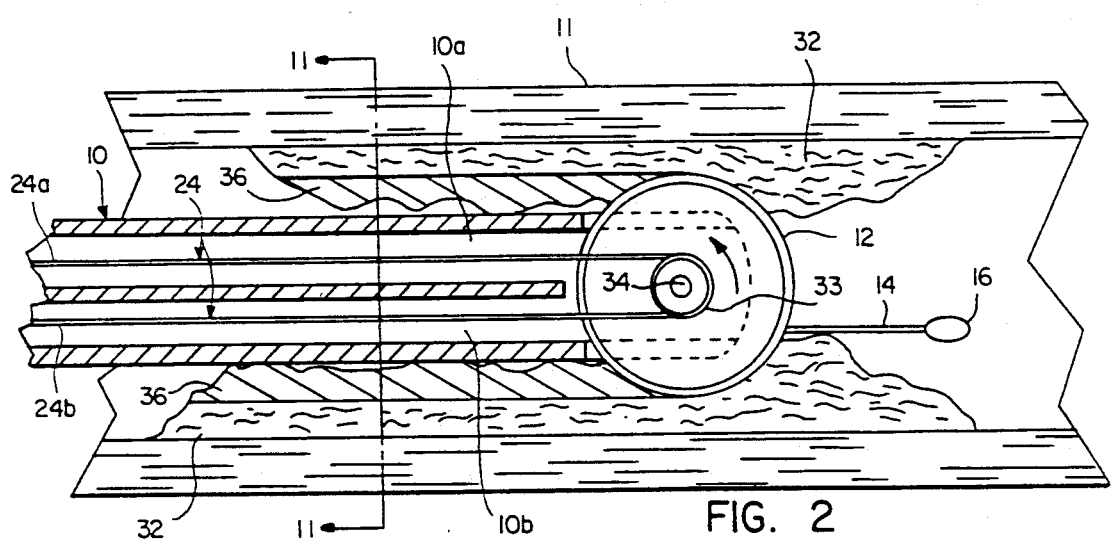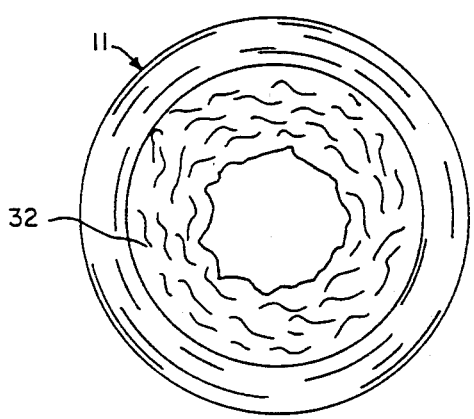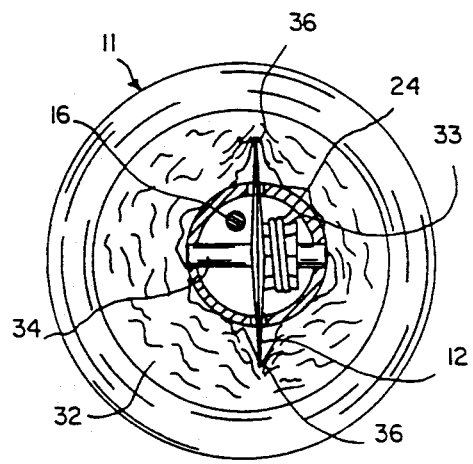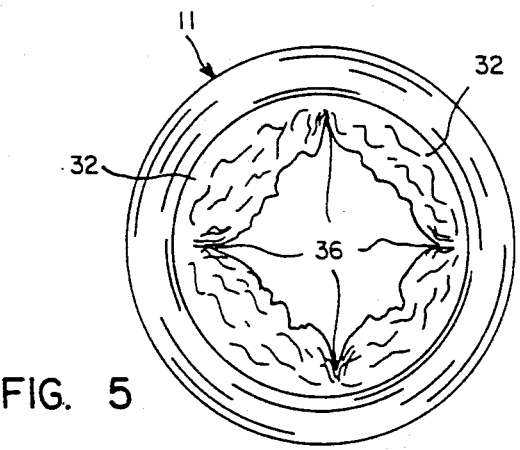

5,059,203

POWERED MICROSURGICAL TOOL

BACKGROUND OF THE INVENTION AND PRIOR ART

This invention relates generally to surgical tools and particularly to powered microsurgical tools of novel construction.

Surgical cutting tools, such as scalpels and saws are well known in the art. Many manual tools have been miniaturized to enable a surgeon to perform minute incisions, often in closely confined areas. A major difficulty with all such tools is that the surgeon must supply the required cutting force by means of a sawing or slicing motion. At best, such miniature tools are restricted to exposed areas of the body to which the surgeon has access or to areas which have been exposed by major surgery.

The novel surgical cutting tool of the invention is powered by a remote drive means and removes the requirement for the surgeon to provide the cutting force. All the surgeon need do is guide the tool. The tool in its fundamental form consists of a rotatable work wheel, i.e. a cutting blade that is mounted at the end of a casing member which in one embodiment includes a rigid tubular section that enables the surgeon to handle it as a conventional scalpel. The tool is also readily adapted to receive a grinding head for abrasive use. In another important version of the invention, the tool is positioned at the end of a miniature flexible catheter for enabling intravascular use, i.e. within the walls of blood vessels such as arteries.

In intravascular surgery, and especially in coronary atherectomies, a catheter coupled device should not endanger the walls of the artery and must be readily flexed around bends while still performing smoothly. Ideally, the tool should be capable of slicing through frontal obstructions or occlusions, not produce loose materials or fragments, and move through the artery with minimal resistance, often while being fed over a guide wire.

The flexibility of the drive system of the invention permits the surgeon to freely manipulate a small slender hand-held tool with relative ease within the proximity of his operating area. The microsurgical tool of the invention is a powerful machine that only requires the surgeon to provide guidance for the tool. In difficult access areas a conventional scalpel often must be held near the end of the handle farthest from the blade. In such a position, every movement of the surgeon's hand is amplified by the length of the scalpel and applying a controlled cutting force is very difficult. With the invention, the powered work wheel (cutting blade) does the work. The cutting blade can be selected to provide a safe, limited depth of cut and eliminate the need for multiple shallow cuts to achieve a desired cut depth as is required with conventional manual scalpels. With the invention, a single clean cut is achieved.

The circular work wheel (blade or abrasive head) of the invention is coupled to a drive hub that rotates about an axis at the distal end of a casing member, which in the preferred embodiments, is a tube or catheter. The surface of the drive hub is treated to improve the grip of a plastic monofilament drive line that extends through the catheter and loops around the drive hub. In the preferred embodiments, the drive hub surface is formed with sharp edges that superficially bite into the monofilament. Also, tensioning is applied to the drive line near the drive hub and the casing member is a multiple or multi lumen device with the pulling (take up) portion and the feeding (payout) portion of the drive line being in separate lumens and maintained out of contact with each other for minimum resistance.

OBJECTS OF THE INVENTION

A principal object of the invention is to provide a novel powered surgical tool.

Another object of the invention is to provide a powered microsurgical tool that is suitable for intravascular use for opening occluded blood vessels.

A further object of the invention is to provide a novel method of opening occluded blood vessels.

A still further object of the invention is to provide an improved balloon angioplasty method.

BRIEF DESCRIPTION OF THE DRAWINGS

These and other objects and advantages of the invention will be apparent upon reading the following description in conjunction with the drawings, in which:

FIG. 2 is a partial cutaway section of a blood vessel showing an occlusion being incised with the tool of the invention;

FIG. 3 is a section of an occluded blood vessel;

FIG. 4 is a section of an occluded blood vessel with the novel tool of the invention making an incision therein;

FIG. 5 is an occluded blood vessel after two incisions with the tool of the invention;

DESCRIPTION OF THE PREFERRED EMBODIMENTS

Figure 1:
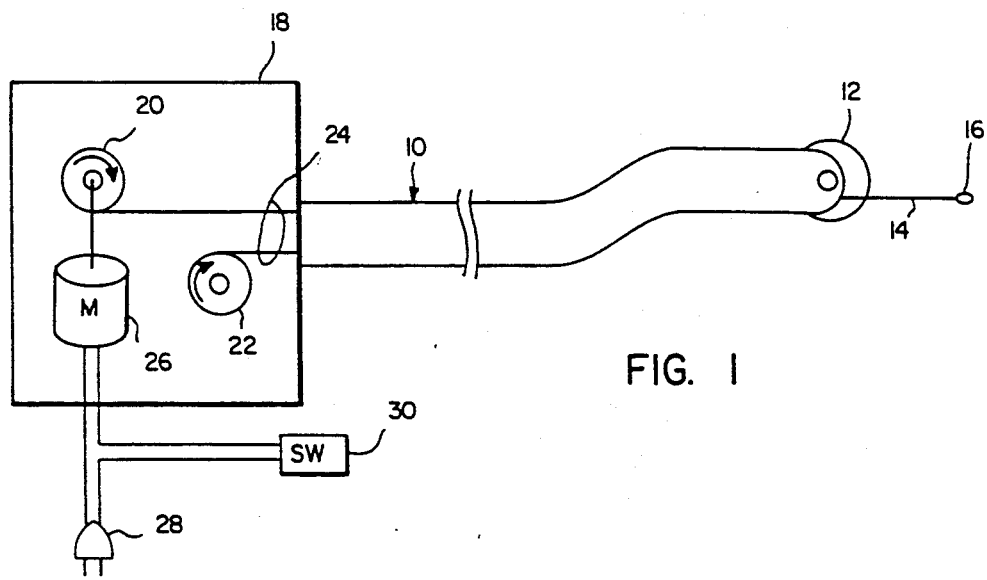
FIG. 1 is a simplified block diagram of a powered microsurgical tool constructed in accordance with one aspect of the invention.

In FIG. 1, a flexible multi lumen catheter 10 includes a rotatable surgical work wheel, in the form of a circular cutting blade 12 mounted at its distal end. The work wheel may also be a circular abrading head. A guide wire 14 including a guide tip 16 extends through catheter 10. A drive unit 18 includes a power take up 20 and a payout 22 for moving a drive line 24 through multi lumen catheter 10 to rotate surgical cutting blade 12. A small motor 26 is drivingly coupled to take up 20 and is coupled to a suitable power source by means of a plug 28. Application of power to motor 26 is controllable by any well known means, such as by a hand or foot operated switch 30. Drive line 24 comprises a plastic monofilament of very small diameter, on the order of light fishing line. Catheter 10 may similarly have a very small diameter to enable its use in human blood vessels and the like.

In FIG. 2, a section of a human artery 11 having an occlusion 32 therein is shown. Guide wire 14, with guide tip 16, is initially threaded through the blood vessel 11 to a point within, and preferably beyond, occlusion 32. Flexible catheter 10, with rotatable cutting blade 12 secured thereto is snaked through vessel 11 over guide wire 14 adjacent occlusion 32. The separate lumens or channels in multi lumen catheter 10 are labelled 10a and 10b, with the tensioned or take up portion 24a of monofilament drive line passing through lumen 10a and the payout portion 24b passing through lumen 10b. This is done to reduce friction, as will be explained. Power is applied to pull take up portion 24a of filament 24 which causes cutter blade 12 to rotate via drive hub 34 and axle 33 for slicing into or incising an occlusion 32 as the catheter is moved by the surgeon. As catheter 10 is moved forward, a clean, single longitudinal incision 36 is made in obstruction 32 by circular cutting blade 12. In accordance with the preferred method of operation, when circular cutting blade 12 is passed through occlusion 32, it is rotated approximately 90° and pulled back through occlusion 32 in the opposite direction to make another longitudinal incision. Thus two longitudinal incisions at 90° to each other are made. These longitudinal incisions disrupt the integrity of the tubular body of the occlusion 32 or plaque, as it is often referred to. Because of the very clean, single pass cut that is made with the microsurgical tool of the invention, the formation of bits and pieces of debris is precluded, which significantly enhances the safety of the tool for arterial work near the heart. Since the occlusion generally has a rubbery-like consistency that is disrupted by the longitudinal incisions, the normal blood pressure in the vessel may suffice to expand the effective interior of the vessel. The plaque may be more easily compressed to expand the flow area in the artery because of the effect of the longitudinal incisions in disrupting the integrity of the plaque. In other cases, further treatment may be required.

As is well known, balloon angioplasty, at least in coronaries near the heart, involves threading a deflated balloon along a catheter guide wire to a position within an occlusion (plaque) and inflating the balloon to compress or compact the plaque material and thus expanding it outwardly against the vessel walls to enlarge the flow area of the artery. This intravascular technique for opening occluded arteries is a quite popular and relatively safe procedure. Unfortunately, because of the consistency of the plaque mentioned above, in many cases the plaque material later expands or "bounces back" to reduce the flow area of the vessel and may completely offset the effect of the balloon angioplasty. The tenacity or integrity of the tubular plaque material is primarily responsible for this later expansion. With the inventive microsurgical tool, the integrity of the plaque material is impaired by slicing it longitudinally, and it is believed that compacting or compressing the plaque outwardly following slicing will offer extended, if not permanent, relief for occluded vessels. Thus an important aspect of the invention is its use in a method of widening the flow area of clogged or occluded arteries by making one or more longitudinal incisions in the plaque material to disrupt its structural integrity, either used alone or in connection with conventional balloon angioplasty, for expanding outwardly the incised plaque material. Thus the use of the invention in opening occluded vessels will greatly benefit intravascular surgery.

Figure 6:
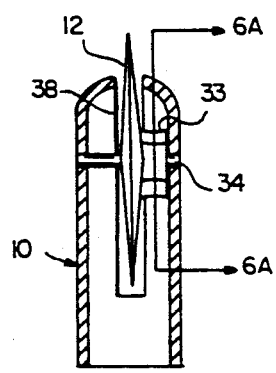
FIG. 6 is a partial view of the casing tip showing the cutting blade, drive hub and axle in place.
Figure 6A:
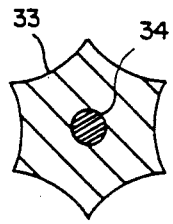
FIG. 6A is a view through the drive hub of FIG. 6 taken along line 6A—6A.

In FIG. 6, a cross section of a circular cutting blade, drive hub and axle mounted in a rounded catheter end is shown. Cutting blade 12, drive hub 33 and axle 34 may be machined from a single piece of stock, although fabricating the parts independently is well within the spirit of the invention. The shape of drive hub 33 is in the form of a pulley to preclude monofilament drive line 24 from tending to ride up the drive hub 33. The surface of drive hub 33 is preferably formed with sharp corners which superficially bite into the monofilament to form a positive drive connection at the cutting blade, i.e. between monofilament drive line 24 and the surface of drive hub 33. These sharp corners are best seen in FIG. 6A. The monofilament drive line may also be looped one or more times around the drive hub 33 to enhance its grip on the hub. A slot 38 is formed in the end of catheter 10 through which circular cutting blade 12 protrudes. The rounded end of the catheter assists in its passage through a blood vessel.

Figure 7:
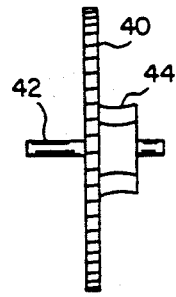
FIG. 7 is a version of a work wheel suitable for abrading material.
Figure 8:
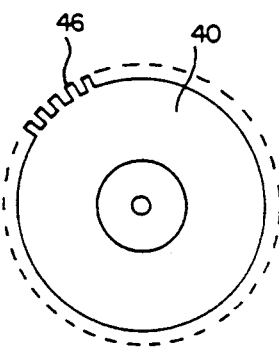
FIG. 8 is a side view of the work wheel of FIG. 7, partially showing the abrading teeth.

In FIG. 7, a configuration for an abrasive type head is shown. A circular abrasive wheel 40 is attached to a drive hub 44 and to an axle 42. As seen in FIG. 8, wheel 40 may include cutting teeth 46 around its periphery similar to a milling cutter. Such a tool is useful for abrading type operations as opposed to slicing operations. A microsurgical tool with an abrasive type head is anticipated to be of great value in the treatment of kidney stones.

Figure 9:
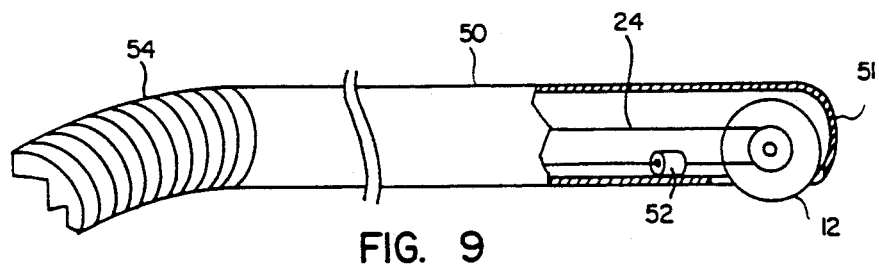
FIG. 9 is a partial view of a hand-held powered surgical cutting tool with a broken away section showing the cutting end.

In FIG. 9, a typical construction of a hand-held powered micro scalpel is shown. A rigid casing 50 is coupled to a flexible tube 54 which in turn is coupled to the power unit (not shown). As indicated in the cutaway portion, the monofilament drive line 24 is passed through a drag means 52 on the inside of casing 50 close to circular cutting blade 12. The provision of the drag means close to the cutting blade minimizes tension in monofilament 24 since it is only in tension between the drag means 52 and take up 20 (section 24a) and substantially free of tension between drag means 52 and payout 22 (section 24b). Drag means 52 may take the simple form of a protrusion that forces a slight change in direction of monofilament 24, thus increasing resistance and tension. An extension of casing 50 forms a hood or cover 51 that extends beyond circular cutting blade 12 and permits cutting at only the lower portion of casing 50. It will be appreciated that casing 50 may take a variety of different forms and be equipped with various type handles to suit the needs of the surgeon. For example, the end of casing 50 may be in the form of a right angle to enable positioning of circular cutting blade 12 as desired by the surgeon. It will also be noted that the very tiny size of the microsurgical tool of the invention cannot be appreciated in the figures, which have been enlarged for the sake of clarity.

Figure 10:
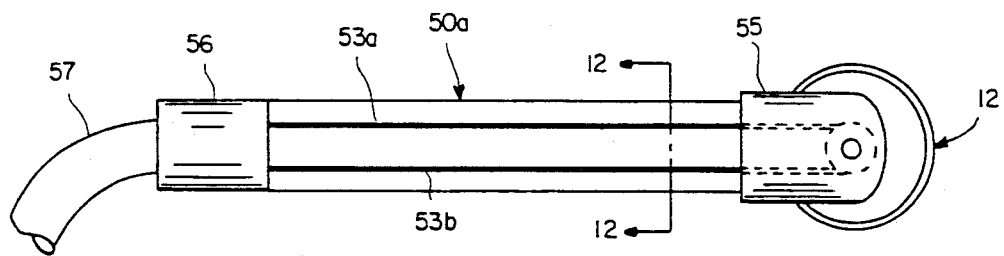
FIG. 10 is a partial view of a different type of hand-held powered surgical tool constructed in accordance with the invention.

In FIG. 10, a different version of a hand-held powered micro scalpel is illustrated. A casing 50a includes a pair of longitudinal slots or grooves 53a and 53b through which monofilament sections 24a and 24b (not shown) pass for driving cutter blade 12. Casing 50a is attached to a support structure 55 that carries cutting blade 12 and an end structure 56 that is coupled to a flexible tube 57, preferably of multi lumen construction. The provision of grooves 53a and 53b allows the monofilament sections 24a and 24b to be isolated (for frictional purposes as discussed above) and out of harm's way while making for a simple readily serviceable tool.

It should be noted that an arrangement of two very light, very flexible, closely wound coil springs may be advantageously used to separate the take up and payout portions of monofilament 24. It has been found that the greatest frictional resistance is due to the oppositely moving sections 24a and 24b of monofilament drive line 24 contacting each other. The smooth walls of the casing (catheter or tube) also introduce friction when contacted by the monofilament drive line, but to a much less pronounced extent. The use of the flexible coil springs is almost ideal since the line contact between the drive line and the casing wall is replaced by a series of point contacts corresponding to the coils of the spring.

Figure 11:
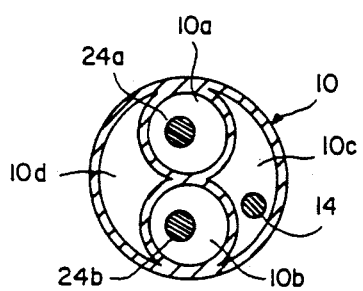
FIG. 11 is a section of the catheter of FIG. 2 taken along line 11—11.

In FIG. 11, a cross section of the multi lumen catheter 10 of FIG. 2 is shown. As shown, the catheter has four orifices or lumens 10a, 10b, 10c and 10d with the different sections of filament 24 being respectively passed through lumens 10a and 10b. Thus section 24a passes through lumen 10a and section 24b passes through lumen 24b. Guide wire 14 is shown in lumen 10c and lumen 10d may be used for fiber optics, fluids or the like, as a matter of choice.

Figure 12A:
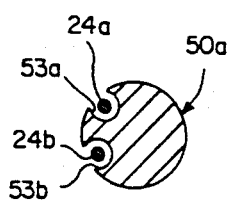
FIG. 12A is a section of the tool of FIG. 10 taken along line 12—12.
Figure 12B:
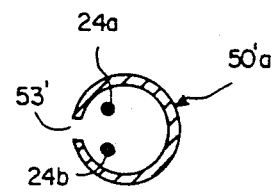
FIG. 12B is a section through another form of casing for the tool of FIG. 12A.

FIG. 12A shows the cross section of casing 50a with slots 53a and 53b housing monofilament sections 24a and 24b, respectively, safe from harm and out of contact with each other. The particular configuration of casing 53a is a matter of choice; its purpose being to provide a rigid support between rotatable blade 12 and the power source (not shown). For example, as shown in FIG. 12B, the casing may be a hollow tube 50a with a longitudinal slot 53', through which monofilament sections 24a and 24b may be introduced. In such an embodiment, the support structure 55 and end structure 56 will need to maintain the separation of the monofilament sections if the friction reduction aspect of the inventive arrangement is to be realized.

Figure 13:
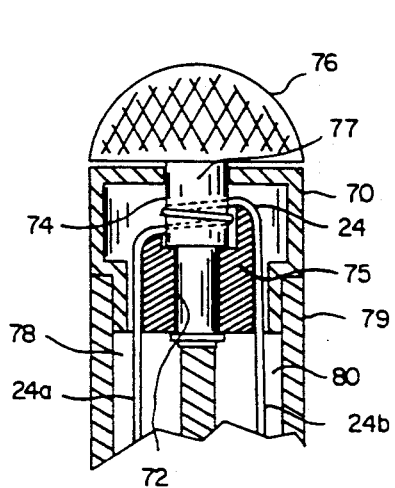
FIG. 13 is an axial drive version of the invention.

FIG. 13 illustrates an on-axis drive arrangement with monofilament drive line 24 being turned 90° by a special guide 75 that is fitted into an end piece 70. Guide 75 is formed with an axial bearing aperture 72 for rotatably securing a milling or grinding type head 76 thereto by conventional means. Monofilament drive line 24 is looped around a mandrel portion 77 of head 76 and sections 24a and 24b pass through lumens 78 and 80, respectively of a multi lumen tube 79. It is important in this arrangement that the monofilament be properly guided around the mandrel 77. This is accomplished by passing the monofilament through guide slots formed in guide 75 with the payout section 24b being displaced from the take up section as shown. This arrangement precludes non-uniform wrapping of the monofilament 24 on the mandrel 77. In practice, guide 75 is press fit into end piece 70, which is secured, in any well known manner, to the end of tube 79.

Figure 14:
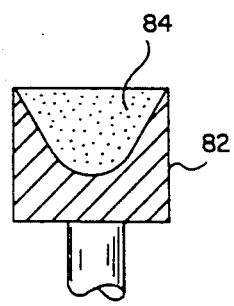
FIG. 14 is a special abrading head for the tool of FIG. 13.

FIG. 14 shows a different shape abrasive head 82 that may advantageously be employed in abrading loose material such as kidney stones. The head 82 includes an inverted cone shaped surface 84 that has the effect of captivating small objects for abrasion.

Figure 15:
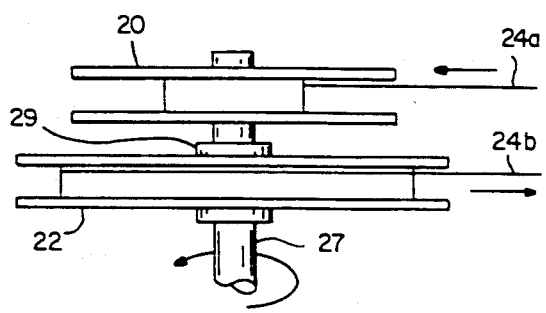
FIG. 15 illustrates a novel low friction drive system for use with the invention.

In FIG. 15, a novel low friction drive system is shown that has particular application in connection with the invention where minimal friction is desired. In this arrangement, take up 20 and payout 22 are mounted on the same shaft 27 that is coupled to a drive motor (not shown). Take up 20 is pinned or otherwise fixed to shaft 27, whereas pay out 22 is freely rotatable thereon, as indicated by a bearing 29. The diameter of take up 20 is smaller than the diameter of payout 22 which means that, in operation, payout 22 will rotate at a slower speed than take up 20 and "slip" (move with respect to) shaft 27. However, the angular speed of take up 20 relative to shaft 27 is significantly less than it would be if take up 20 was separately mounted for rotation. Thus the effect is that the friction in bearing 29 is much lower and a relatively low cost bearing arrangement may be used to obtain a high quality frictionless bearing. Since it is anticipated that the invention will find extensive use in health care facilities where, for any number of reasons, disposal is preferred to sterilization and reuse, the low cost, high performance drive will be of significant benefit.

It is anticipated that a wide variety of casing sizes and work wheel configurations will be required to suit the needs of the surgeon. The hand-held microsurgical tool will be preferably coupled to a three or four foot flexible double coil spring catheter as described in FIG. 10, thus providing the surgeon with a wide range of easy movement. As mentioned, a switch for controlling operation of the surgical tool may be mounted on the handle for fingertip control or it may be a foot operated switch. Such details are considered well within the skill of those in the art and are not to be considered limitations of the invention. The invention is to be limited only a defined in the claims.

What is claimed is:
1. A powered miniature tool comprising:
work wheel means having an axis of rotation;
a casing member having a proximal end and a distal end;
means supporting said work wheel means for rotation about said axis adjacent said distal end of said casing member;
a flexible filament drive line within said casing member for imparting rotational movement to said work wheel means; and
drive means coupled to said flexible filament drive line adjacent said proximal end of said casing member.

2. The tool of claim 1, further including bearing means at said distal end of said casing member for supporting said work wheel means about said axis.

3. The tool of claim 2 wherein said work wheel means includes a circular work wheel, a drive hub and an axle, said drive hub including grip means and wherein said flexible filament drive line comprises a plastic monofilament that is looped about said drive hub and wherein said casing member includes friction reducing means for reducing loading of said monofilament.

4. The tool of claim 3, further including drag means close to said drive hub for tensioning said monofilament.

5. The tool of claim 4 wherein said casing member has an outer periphery, said circular work wheel extending partially beyond said outer periphery.

6. The tool of claim 4 wherein said casing member is a flexible tube, and further including a guide wire in said flexible tube extending beyond said distal end of said flexible tube alongside said circular work wheel for guiding said flexible tube into a vessel.

7. The tool of claim 3 wherein said monofilament includes individual strands in said casing member and wherein said casing member is tubular and includes a plurality of sections for separating said individual strands of said monofilament.

8. A powered miniature tool comprising:
a circular work wheel including a drive hub and an axle;
a casing member having a proximal end and a distal end;
bearing means supporting said axle in said distal end of said casing member;
a flexible monofilament drive line including pay out and take up strands in said casing member, and being coupled to said drive hub for imparting rotational movement to said circular work wheel;
motor drive means coupled to said flexible monofilament drive line adjacent said proximal end of said casing member; and
means for minimizing frictional loading on said flexible monofilament drive line in said casing member.

9. The tool of claim 8 wherein said casing member comprises a multi lumened tube with said pay out and take up strands of said monofilament being in different lumens for minimizing said frictional loading.

10. The tool of claim 9, further including a flexible multi lumened tubular member coupled between said motor drive means and said multi lumened tube.

11. A powered miniature surgical cutter comprising:
a multi lumened tube having a proximal and a distal end;
a circular blade, a drive hub and an axle mounted at said distal end of said tube;
said circular blade having a diameter such that at least a portion thereof extends beyond the wall of said tube;
a monofilament drive line coupled to said drive hub via one lumen of said tube and extending back through said tube via another lumen;
means near said distal end of said tube for tensioning said monofilament drive line; and
means at said proximal end of said tube for pulling said monofilament drive line to rotate said circular blade.

* * * * *